United States Patent [19]

Robichaud et al.

[11] Patent Number: 6,078,181
[45] Date of Patent: Jun. 20, 2000

[54] METHOD FOR THE MEASUREMENT OF FOREST DUFF MOISTURE CONTENT

[75] Inventors: Peter R. Robichaud, Moscow, Id.; Roger D. Hungerford; David S. Gasvoda, both of Missoula, Mont.

[73] Assignee: The United States of America as represented by the Secretary of Agriculture, Washington, D.C.

[21] Appl. No.: 09/246,272

[22] Filed: Feb. 8, 1999

Related U.S. Application Data

[62] Division of application No. 08/769,021, Dec. 18, 1996, Pat. No. 5,920,195.

[51] Int. Cl.[7] .................................................. G01R 27/26
[52] U.S. Cl. .......................... 324/643; 324/689; 324/696; 73/73
[58] Field of Search ................................ 73/73; 324/696, 324/689, 643, 640, 634, 535

[56] References Cited

U.S. PATENT DOCUMENTS

| | | |
|---|---|---|
| 3,789,296 | 1/1974 | Caruso, Jr. et al. . |
| 3,979,947 | 9/1976 | Parkinson ..................................... 73/73 |
| 4,341,112 | 7/1982 | Mackay ........................................ 73/73 |
| 4,786,857 | 11/1988 | Mohr et al. . |
| 4,918,375 | 4/1990 | Malicki et al. . |
| 5,136,249 | 8/1992 | White et al. . |
| 5,341,673 | 8/1994 | Burns et al. . |
| 5,376,888 | 12/1994 | Hook . |
| 5,420,517 | 5/1995 | Skaling et al. . |
| 5,646,537 | 7/1997 | Skaling ................................... 324/643 |
| 5,663,649 | 9/1997 | Topp ....................................... 324/643 |
| 5,726,578 | 3/1998 | Hook ....................................... 324/643 |
| 5,920,195 | 7/1999 | Robichaud .............................. 324/643 |

*Primary Examiner*—Josie Ballato
*Assistant Examiner*—Jose M. Solis
*Attorney, Agent, or Firm*—Janet I. Stockhausen; M. Howard Silverstein; John D. Fado

[57] ABSTRACT

An apparatus and method for the moisture content measurement of compressible materials using pressure to firmly hold surface probes against the material to be measured. The apparatus uses moisture measurement circuitry employed in frequency domain impedance or time domain reflectometry devices to obtain moisture content readings from materials. These moisture content readings are based on the apparent dielectric constant of the measured material. Subsurface air voids or gaps found in loose, layered materials undesirably influence moisture measurement readings by reducing the apparent dielectric constant of the measured material. Pressure is supplied through the apparatus to the material in the proximity of the surface probes, thereby reducing air voids to enhance measurement accuracy. The apparatus and method are especially useful for compressible organic materials such as forest duff, hay and soil.

1 Claim, 5 Drawing Sheets

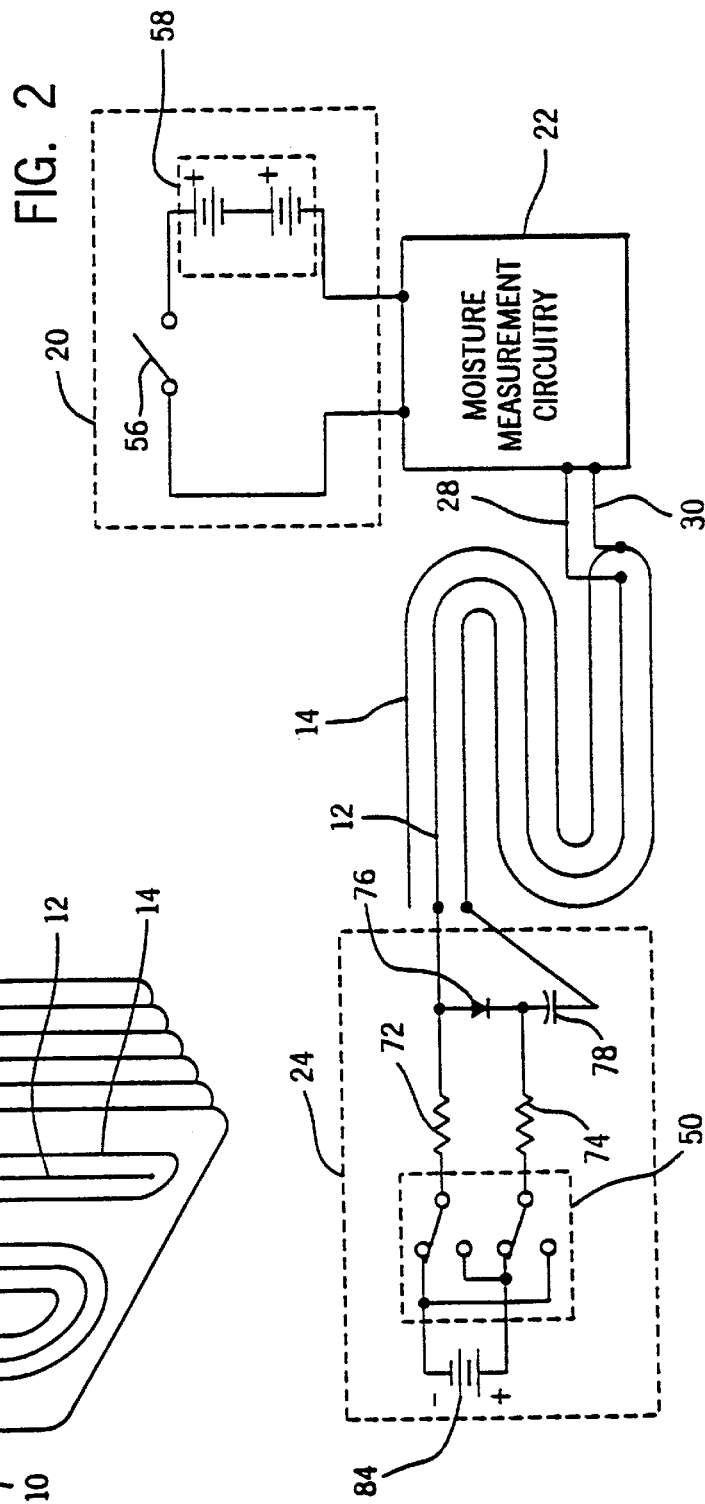

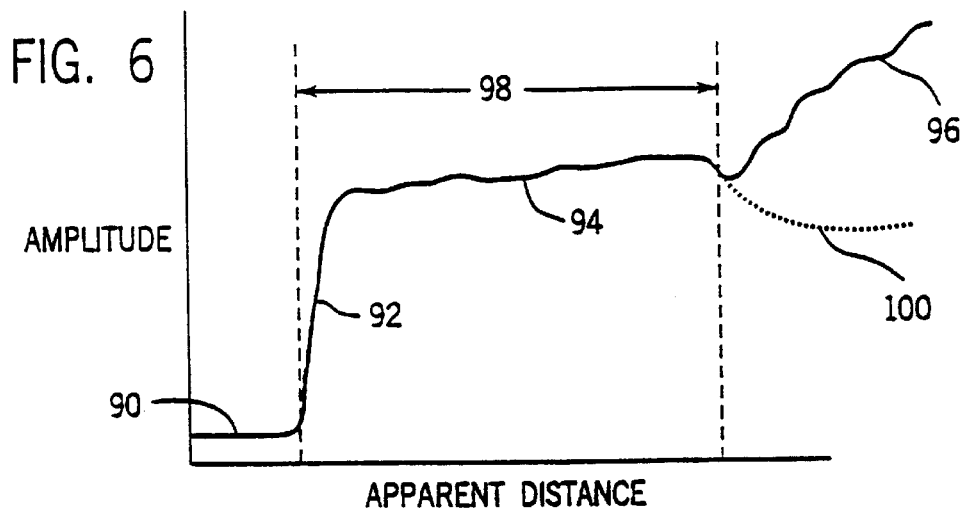
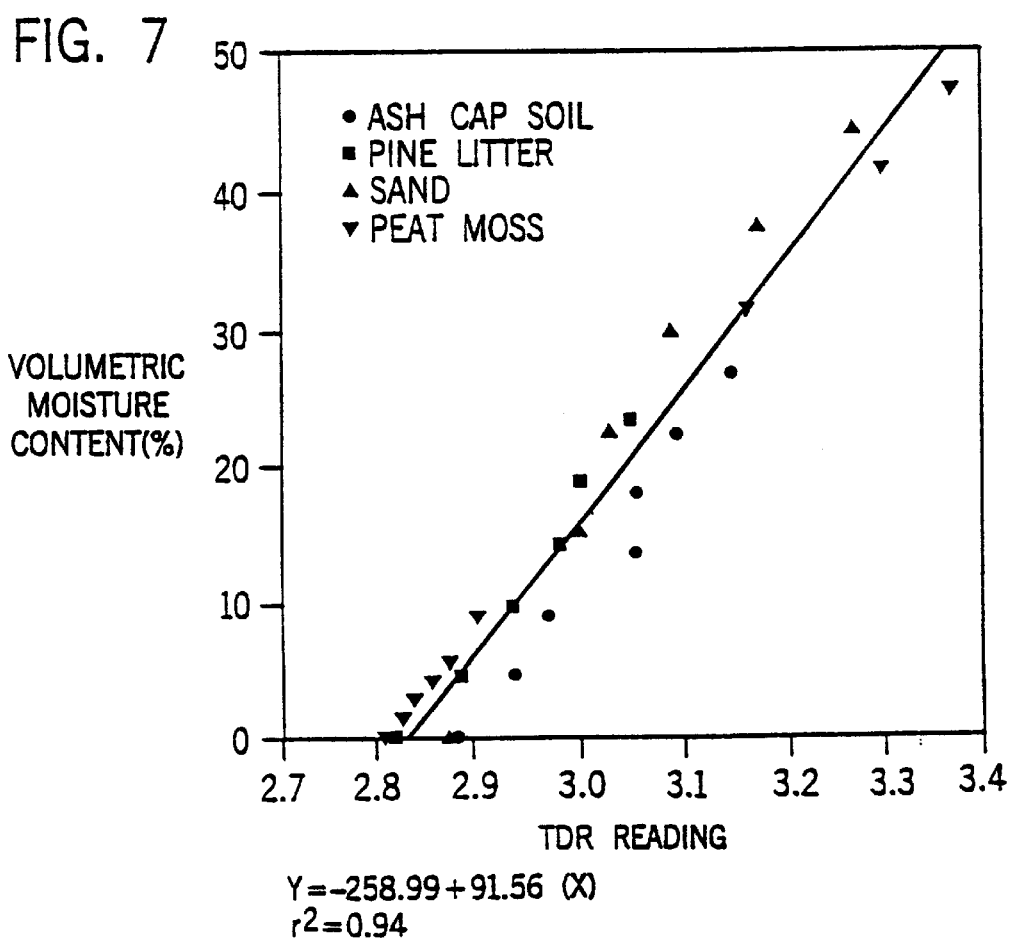

METHOD FOR THE MEASUREMENT OF FOREST DUFF MOISTURE CONTENT

This application is a divisional of U.S. patent application Ser. No. 08/769,021, filed Dec. 18, 1996 now U.S. Pat. No. 5,920,195.

FIELD OF THE INVENTION

This invention relates generally to moisture measurement devices and more particularly, relates to a portable method and apparatus that provides real-time moisture content measurements of compressible solids such as forest duff.

STATEMENT REGARDING FEDERALLY SPONSORED RESEARCH AND DEVELOPMENT

BACKGROUND OF THE INVENTION

Fire is a natural component of forest and wildland ecosystems. Fires, whether caused by humans or lightning, can be devastating. Trees may be killed, shrubs providing food and cover for wildlife are reduced to ashes, and grasses or forest floors are burned away leaving the soil bare for the effects of erosion. However, fire used as a land management tool can be most beneficial. Prescribed burning is used to reduce the heavy buildup of fuels such as woody debris, provide nutrients to the soil, prepare areas for planting, restore tree stands, and create wildlife habitats.

Forest fires are greatly influenced by the moisture content of the forest floor. The forest floor is a nonhomogenous solid comprised of several layers. The top layer is the non-decomposed material consisting of twigs, grasses, leaves, pine needles and other dead debris. Next, is the duff region that is both a partially decomposed layer of organic material often bound with fungus, then an extensively decomposed layer. One may find many air voids in the duff region, which can vary in bulk density. The duff region also can vary in thickness from approximately two to twenty centimeters.

Fire can burn along the duff at either a slow or fast rate and the amount of duff region consumed by the fire is a function of the duff region's thickness and moisture content. An ideal system would allow managers to take real-time measurements of duff moisture content in the field. A portable moisture measurement system will aid land managers on the timing of prescribed burns, and aid wildfire managers in predicting fire behavior characteristics.

Duff moisture content is difficult to measure in the field using traditional techniques. Typically, a duff sample is taken in the field and sealed in an air-tight container. The sample is transported to a laboratory where it is weighed before being oven-dried at 85 degrees centigrade for 24 to 48 hours. Moisture content is then calculated using the field and oven-dry weights.

Time is critical when managers are faced with a wildfire situation, therefore, traditional duff moisture measurement methods taking at least 24 hours are inadequate. An instrument that can instantaneously provide duff moisture content greatly aids in the prediction of fire behavior as it relates to duff consumption. Effective fire behavior prediction would allow fire managers to better allocate fire-fighting resources to critical fire areas.

Currently, moisture content is not used in the predictive model for prescribed fire behavior because of the time it takes for measurement. However, real-time moisture content information would increase modeling accuracy in predicting the behavior of the prescribed burns and give more flexibility for users of this valuable conservation tool.

Moisture measurement circuitry, such as time domain reflectometry (TDR) and frequency domain impedance circuitry, operates by measuring the change in dielectric constant and is useful for moisture content measurements TDR measuring systems produce discrete electrical pulses that travel through and react with the medium resting against the electrodes. Basically, these electrical pulses travel at a velocity directly dependent on the dielectric constant of the surrounding medium; the higher the dielectric constant, the slower the electrical pulses will travel. This dielectric constant is dependent on the water and air void content of the measured medium. The measurement accuracy may also be affected by saline content, but in the application of duff measurement, this factor is unlikely to be present. Therefore, one can ascertain using time domain reflectometry techniques the changes in propagation velocity of the discrete electrical pulses traveling the length of the electrodes, and the velocity change can be directly correlated with the moisture content of the medium against which the electrodes rest.

Time domain reflectometry (TDR) has been used for moisture content measurements for years; therefore, prior inventions exist for the measurement of soil moisture content. (For example, refer to FIG. 1a depicting how a typical TDR probe is used for soil moisture content measurements.) However, prior inventions lack features that make these analysis techniques accurate for use with compressible materials such as forest duff.

SUMMARY OF THE INVENTION

The present invention provides a portable apparatus employing surface probes that, when combined with moisture measurement circuitry, can provide real-time moisture content measurements of a compressible medium like forest duff.

Electronic means of determining the moisture content of a wide variety of materials have been proven successful. Examples of moisture measurement circuitry readily available are time domain reflectometry and frequency domain impedance measuring devices. The present invention uses electrodes to put electrical signals produced by such devices in contact with the material to be measured. At least two electrodes will operate as surface probes, and shall be affixed to an electrode carrier surface. The electrodes are spaced apart, and arranged into a S-shaped pattern. If three electrodes are used, the outer two shall be electrically connected at one end. This three-electrode configuration ensures that the electric field is evenly distributed over the material so all portions of the sampled material contribute equally to the measurement. Thus it is one object of this invention to provide surface probes that are compactly designed and operable with TDR or frequency domain impedance devices.

The moisture measurement circuitry is used in conjunction with output display circuitry. The output display provides the user with the instant information provided by the moisture measurement circuitry. Thus it is another object of the invention to display real-time moisture measurements.

The electrode carrier surface is affixed to a support frame using a force sensitive coupling. For instance, an air bellows may be connected between the support plate and electrode carrier surface, and a pressure sensitive switch can perform the electrical activation of the moisture measurement circuitry. Thus it is another object of the invention to distribute force evenly over the electrode carrier surface and obtain moisture measurements at a pre-determined pressure resulting from the distributed force.

Because the present invention can be transported into the field for use, it is yet another object of this invention to provide a handle that may serve not only as a carrier, but provide to the user a means to apply force to the support frame.

When the present invention is used with TDR moisture measurement circuitry that requires the user to measure the physical length of the moisture measurement output, the present invention includes a diode shorting circuit. The diode shorting circuit affects the moisture measurement output, embodied as a wave trace, so one may easily estimate where to end measurement. Thus it is yet another object of the present invention to activate the moisture measurement circuitry and virtually short the electrodes to provide a timing marker for TDR measurements using a diode connected to a pressure sensitive switch.

It is finally another object of the present invention to provide a method for the moisture content measurement of compressible organic materials such as forest duff using the apparatus of the present invention.

The present invention can be used to measure the moisture content of compressible organic materials such as forest duff. It will be understood that although the apparatus will be described in relation to specific measurement applications, the apparatus according to the invention is not limited to use for such applications.

BRIEF DESCRIPTION OF THE DRAWINGS

FIG. 2 is a schematic block diagram showing optional circuitry for first and second embodiments;

FIG. 3 is a perspective view of the bellows system specifically showing the inner and outer electrodes;

FIG. 6 is a typical TDR wave trace;

FIG. 7 is a graph portraying typical correlation between the TDR value and volumetric moisture content for mediums of varying bulk density.

DETAILED DESCRIPTION OF THE PREFERRED EMBODIMENTS

Figure 1A:
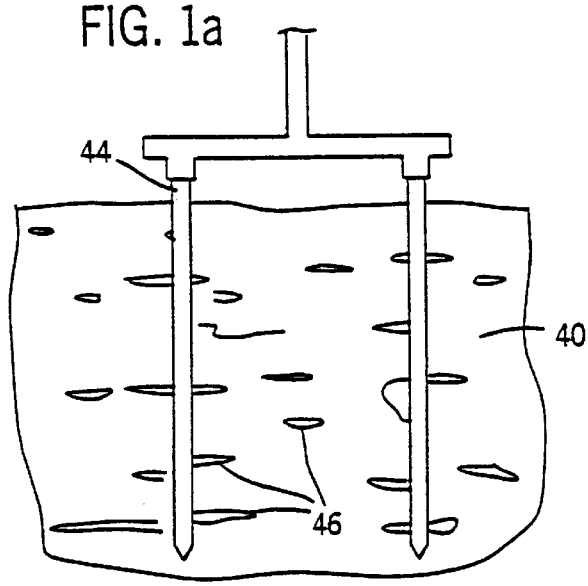
FIGS. 1a–1d show: conventional TDR probes inserted into a medium; the compression of air voids when pressure is applied using present invention; cutaway perspective views of a medium, said medium being measured using the present invention; and layers of forest material.

The present invention recognizes that compressible materials contain extraneous air voids that distort the electrical field produced by moisture measurement circuitry and result in spurious moisture content measurements. This is because the moisture content readings are dependent on the material dielectric constant, and the constants for air and water are very different. As demonstrated in FIG. 1a, it is impossible to determine how many subsurface air voids 46 are contacting conventional moisture measurement probes 44. Therefore, it is advantageous to use surface probes to measure a compressible material containing air voids because one can prepare the surface to improve contact with the probes.

Figure 1B:
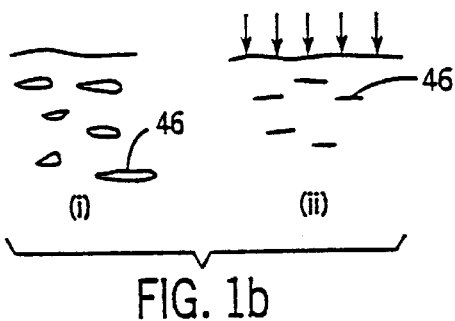

The use of surface probes does not fully solve the problem of subsurface air voids because the probe's electrical signal penetrates down into the material in the proximity of the electrodes. Spurious readings may still result. Therefore, the remedy the present invention presents in addition to surface electrodes is to press the apparatus against the material to be measured at a pre-determined pressure. Shown in FIG. 1b(i) is a material with subsurface air voids 46, and shown in FIG. 1b(ii) is the closing effect downward pressure can have on subsurface air voids 46. Downward pressure will also provide better surface contact because compressible materials will conform to the surface of the apparatus.

a. General Operation of the Moisture Measurement Apparatus

Schematically shown in FIG. 2 is the apparatus used for measuring the moisture content of materials. The electrical components of the apparatus are basically comprised of at least two electrodes and moisture measurement circuitry 22. There exists two embodiments for the present invention that are distinguished by the type of moisture measurement circuitry 22 each employs. For the required moisture measurement circuitry 22, the first embodiment employs a frequency domain impedance device. This device is used in conjunction with first embodiment circuitry 20. For the required moisture measurement circuitry 22, the second embodiment employs a time domain reflectometry device. This device is used in conjunction with second embodiment circuitry 24.

Referring to FIG. 3, a perspective view is shown of the electrode array affixed to the bottom of apparatus 10. Preferably, the present invention uses three parallel, coplanar electrodes, spaced evenly apart and arranged into an S-shaped pattern for compactness. The electrodes are constructed out of an electrically conductive material, such as tin-plated copper. The outer electrodes are electrically connected at one end to create two electrodes, specifically one inner electrode 12, and one outer electrode 14. Greater electrical measurement sensitivity results when three electrodes are formed into two electrodes.

Measurement sensitivity is influenced by the penetration depth of the electrical field emanating from the electrodes, the depth being dependent on the spacing between electrodes. Also, the material closest to the electrodes has a greater effect on measurement than material farther from the electrodes. For example, probes spaced 1.2 centimeters apart, sixty percent of the measurement is from the material located within the first 0.38 centimeters from the probe, and ninety percent from within the first 0.76 centimeters.

The electrodes are flushly attached to the electrode carrier surface so one may keep the surface clean and dry for precise measurement. Using typical circuit board fabrication methods provides a satisfactory means for embedding the electrodes to the electrode carrier surface 16. Preferably, the electrode carrier surface 16 is made from a stock Teflon circuit card characterized by its ability to withstand intended use yet conform slightly to the measured material's surface, support electrical circuitry, be cleaned easily, and display a low dielectric constant.

Figure 4:
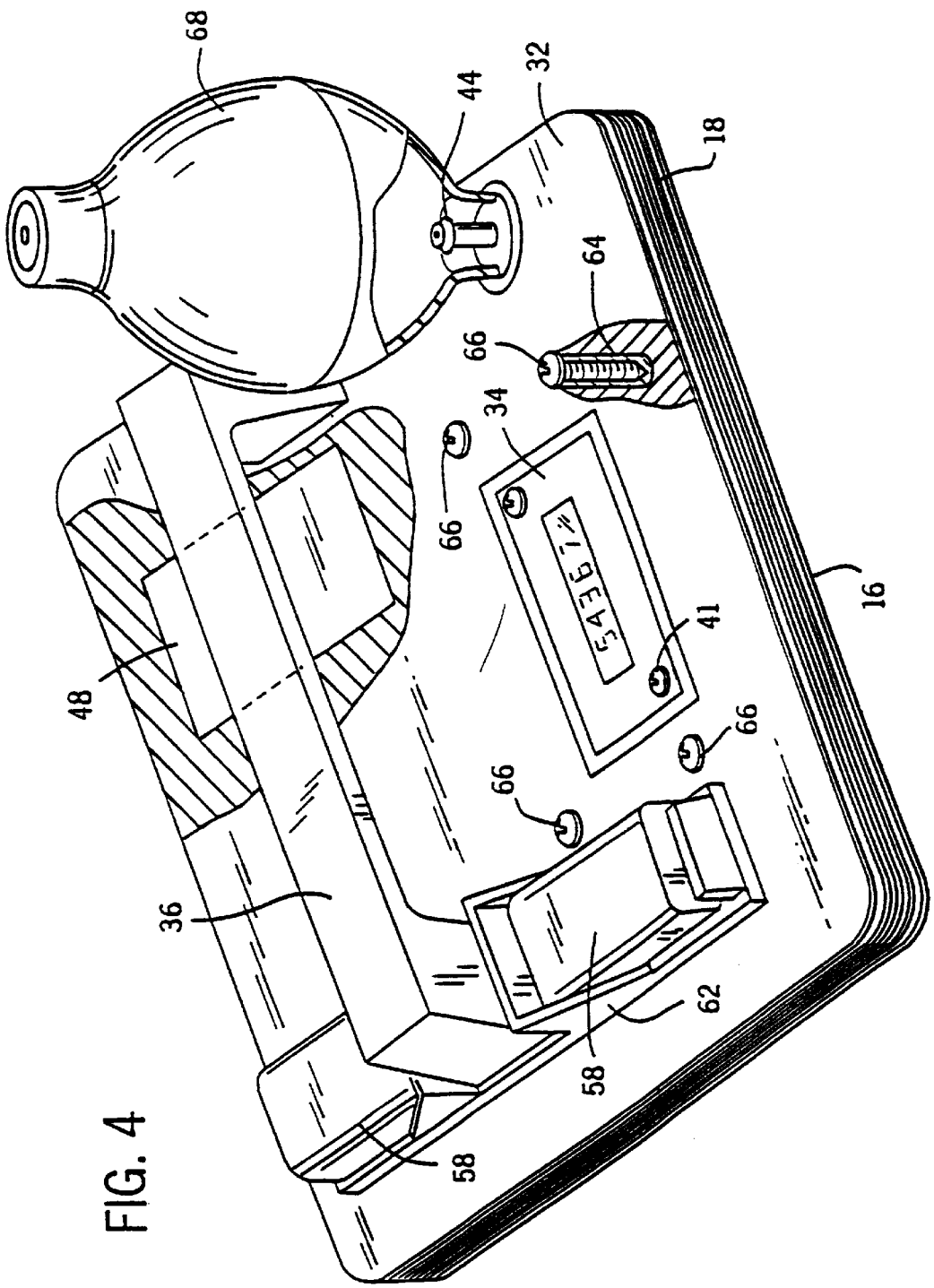
FIG. 4 is a cutaway perspective view of the moisture measurement system in accordance with the first embodiment, showing by cutaway the interior moisture measurement circuitry, a one-way check valve attached to a detachable air pump, and a screw-mounted post.

Referring to FIGS. 3 and 4, one may view the force sensitive coupling 18 and support frame 32. The force sensitive coupling 18 is attached to the perimeter of the electrode carrier surface 16 on the side opposite of the electrodes. This force sensitive coupling 18 is preferably attached with an adhesive and constructed of a nonpermeable yet flexible material such as a rubber air bellows, characterized by its ability to accommodate applied pressure, maintain a fold, and withstand repeated folding. The free end of the force sensitive coupling 18 is then attached to the support frame 32, thereby creating a sealed volume contained between the two parallel surfaces of electrode carrier surface 16 and support frame 32. Again, adhesive is the preferable means for attachment.

By creating a sealed volume with a force sensitive coupling 18, a uniform pressure 38 may be translated from the apparatus 10 to the measured medium by applying a downward force 26 to support frame 32. (See FIG. 1c). Specifically, this downward force 26 is applied by pressing the handle 36 mounted on top of the support frame 32. The uniform pressure 38 will compress the measured medium in the proximity of the electrodes. Uniform pressure could be achieved using springs rather than rubber air bellows but bellows provide uniform pressure more effectively because fluids, such as air, intrinsically distribute pressure equally.

Described below are two different embodiments of the present invention. The first embodiment is a portable self-contained system that operates using a frequency domain impedance device. The second embodiment, though still portable, is not self-contained because it requires auxiliary time domain reflectometry equipment.

i. The First Embodiment

Referring generally to FIGS. 2 and 4, illustrated is one preferred embodiment of the apparatus 10. The moisture measurement circuitry 22 is comprised of a frequency domain impedance device (not shown) Electrical signals from the impedance device propagate through the electrodes, which couple with the measured material. It is known that the measured capacitive impedance component is related to the moisture content of the material in the proximity of the electrodes. Therefore, the impedence is related to the measured medium's moisture content using a calibration equation.

Referring to FIG. 4, this first embodiment of the present invention has two advantages over its second embodiment: (1) it is very portable and (2) the user can obtain real-time numerical output representing the moisture content of the measured material. For portability and protection from the elements, the moisture measurement circuitry card 48 is housed within the sealed volume between the support frame 32 and the electrode carrier surface 16.

The assembly of the moisture measurement circuitry 22 within the sealed volume is described. First, the electrode connections pass through the electrode carrier surface 16 to the interior of the sealed volume. The connection between the electrodes and moisture measurement circuitry 22 consists of two leads: a first-lead 28 connected to inner electrode 12, and second-lead 30 connected to electrode 14. Second, the moisture measurement circuitry 22 is attached to the inner surface of electrode carrier surface 16, preferably with a double-backed adhesive foam tape that can serve to absorb mechanical shock and allow for any flexing of electrode carrier surface 16. Finally, the output display 34 is electrically connected to the other moisture measurement circuitry, then attached to the underside of the support frame 32 using screws 41 such that the LCD display is visible to the user. The support frame 32 should be made from a clear, rigid material such as acrylic to allow the user to view interior components without creating unnecessary apertures FIG. 2 shows a schematic of the first embodiment circuitry 20. This additional circuitry is used to achieve the objective of obtaining moisture measurements at a pre-determined pressure. To meet this objective, this embodiment of the invention uses a single-pole pressure switch 56 resting in the open-circuit position. This pressure sensitive switch responds to the pressure within the sealed volume. When enough pressure is applied to close is the circuit, electrical power is supplied, preferably with DC batteries or alternative power to activate the moisture measurement circuitry 22 and output display 34. The primary purpose of taking measurements at a pre-determined force is to ensure test repeatability. In addition, it informs the user when enough pressure has been applied to the system.

The physical attachment of the first embodiment circuitry 20 to the apparatus 10 is depicted in FIG. 4. First, the electrical power source 58, possibly DC batteries and battery mounts 62, is mounted on the top-side of the support frame 32 using screws or adhesive. Next, the single-pole pressure switch 56 (not shown) is mounted over a sealable aperture in the support frame 32. Leads (not shown) from the power source 58 and single-pole pressure switch 56 (also not shown) are threaded through appropriately placed sealable apertures in the support frame 32. Lastly, all apertures created to accommodate leads, screw attachments or components are sealed using a silicone adhesive or similar product.

Apparatus 10 deflates over time due to use. Referring to FIG. 4, over deflation that could result in internal component damage is prevented with internally located screw-mounted posts 64 of equal height, perpendicularly mounted with respect to the plane of support frame 32, using screws 66. Four posts 64 are arranged at each corner of the output display 34, and other posts are strategically located to prevent damage elsewhere. When bellows system 26 is deflated completely, all posts 64 should contact only the inside surface of electrode carrier surface 16 to prevent interior components from being damaged. All apertures created to accommodate posts 64 are sealed, preferably with a silicone adhesive or similar product.

When needed for use, the apparatus 10 may be inflated by means of an optional and detachable inflation device 68, preferably a rubber bulb which can urge air into the into the sealed volume through a one-way check valve 44. The inflation device 68 is squeezed repeatedly until desired bellows height is obtained. Without the optional inflation device 68, inflation is obtained by grasping the edges of the electrode carrier surface 16 and handle 36, while gently pulling apart until desired inflation results.

ii. The Second Embodiment

Figure 5:
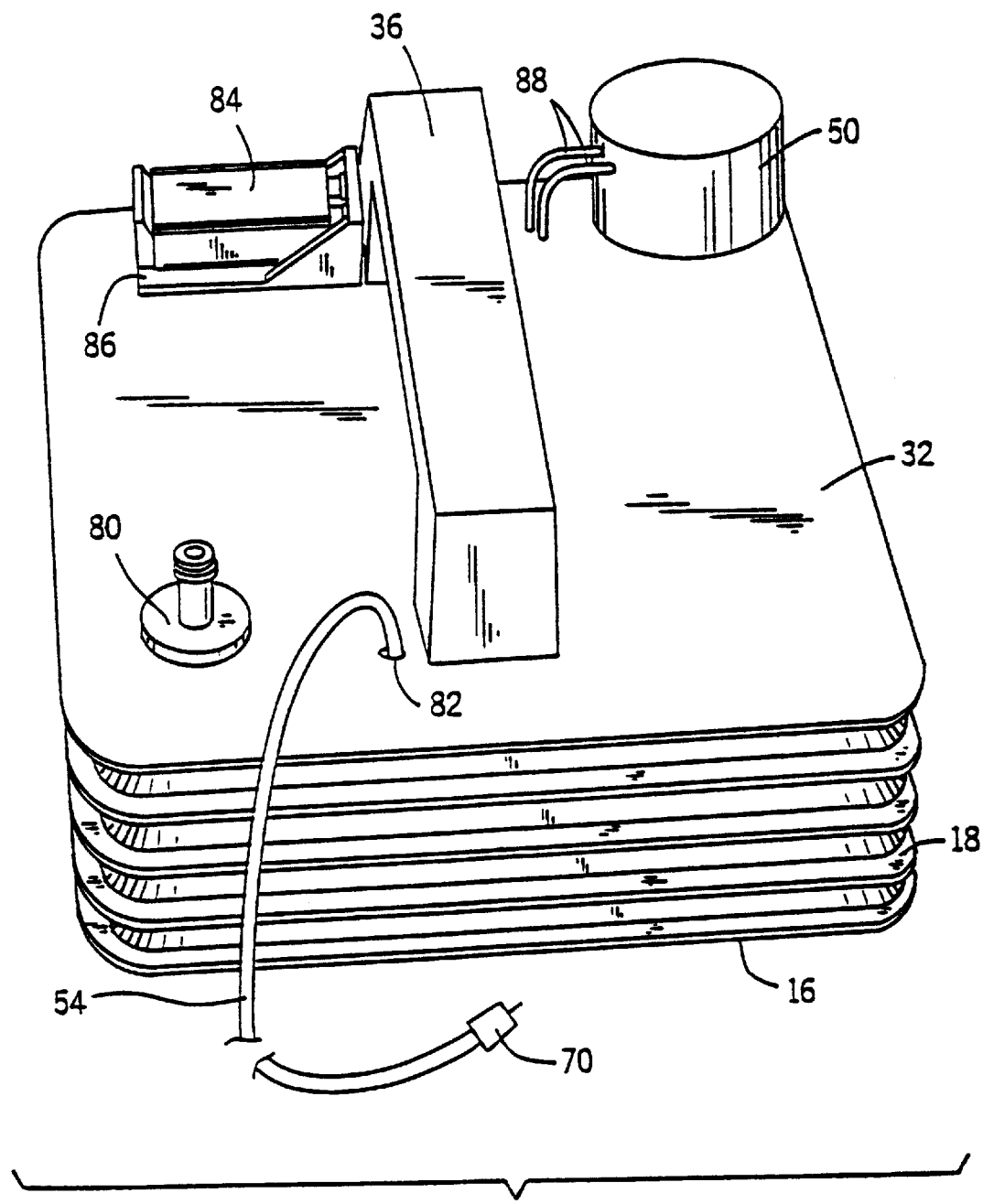
FIG. 5 is perspective view of the moisture measurement system in accordance with the second embodiment.

In another preferred embodiment of the invention depicted in FIGS. 2 and 5, one may appreciate the option of using the apparatus 10 with an external TDR device, such as a Tektronix 1502C TDR unit. Shown in FIG. 5, the coaxial line 54 connects electrodes to the TDR unit using a BNC type connector 70. The coaxial line 54 shield foil (not shown) is electrically connected with outer electrode 14, and the coaxial line 54 center conductor (not shown) with inner electrode 12. The electrical connections between coaxial line 54 and electrodes are located on the inner side of electrode carrier surface 16. Therefore, coaxial line 54 must pass upward through a sealable aperture 82 in the support frame 32 for connection with an external TDR device. This aperture 82 is preferably sealed with a silicone adhesive or similar product, when the force sensitive coupling 18 is fully extended. This allows one to expand the force sensitive coupling 18 freely for use without damaging the internal coaxial line connection.

As in the first embodiment, the apparatus 10 tends to deflate with use over a period of time. If necessary, the sealed volume between support frame 32 and electrode carrier surface 16 may be inflated with attached inflation device 68 (as seen in FIG. 4 of the first embodiment) to the one-way check valve 80. Without an inflation device, inflation is obtained by grasping the edges of the electrode carrier surface 16 and handle 36, while gently pulling apart until the desired inflation results.

The second embodiment requires second embodiment circuitry 24 as shown in FIG. 2. This additional circuitry fulfills the objective of activating the moisture measurement circuitry 22 at a pre-determined force. Specifically, this objective is achieved using a double-pole, double-throw pressure sensitive switch 50, connected in series with a power source 84, such as a DC battery. The pressure sensitive switch responds to the pressure within the sealed volume. The double-pole, double-throw pressure sensitive switch 50 not only serves to inform user that the appropriate force for measurement has been applied to apparatus 10, when used in conjunction with the diode shorting circuitry described below, it also assists the user in defining the measurements taken from TDR traces (shown in FIG. 6).

The diode shorting circuitry is shown schematically in FIG. 2. Resistors 72 and 74 are electrically connected to each pole of the double-pole, double-throw pressure switch 50, and serve to both limit the current entering the forward-biased diode 76 (hereinafter diode 76) and to isolate second embodiment circuitry 24. A Schottky Barrier diode—UHF mixer/detector, or a PIN diode designed for general purpose UHF switching will satisfy the diode 76 requirement. It shall be noted that the double-pole, double-throw pressure sensitive switch 50 operates to reverse the bias from the power source 84, such that when pressure is applied, the diode experiences a forward bias. The resistor 72 is connected to the diode 76 anode, and resistor 74 to the diode 76 cathode. The diode 76 anode is also connected to the inner electrode 12, and diode 76 cathode to capacitor 78. The capacitor 78 prevents the direct current in the second embodiment circuitry 24 from entering the electrodes and the TDR moisture measurement circuitry. Specifically, the capacitor 78 is a low impedance path to the TDR pulse; when diode 76 is forward biased, a low impedance path is presented across the end of the electrodes and a virtual short circuit occurs. This low impedance path follows through the forward biased diode 76 and capacitor 78.

Illustrated in FIG. 6 is the influence of the diode shorting circuit as it pertains to TDR trace analysis. A typical TDR trace begins with a constant amplitude 90 representing the coaxial cable, a pulse increase 92 representing the beginning of the electrodes, a nearly steady amplitude 94 representing the electrode length, and an upward slope 96 representing the end of the electrodes. The upward slope 96 occurs when the diode is reverse biased. The final downward slope 100 occurs when the diode is forward biased. The intersection of the upward slope 96 and downward slope 100 accurately indicates the end of the probe. The upward slope 96 is not always as abrupt as illustrated and locating the end of the probe is difficult without employing a diode switch.

The apparent probe length 98 between the beginning and end of the pulse represents travel time through the electrodes, and is used to determine the ratio of the actual probe length to the apparent probe length 98. This ratio can be used to calibrate the apparatus 10 readings with known moisture contents by employing a linear regression analysis.

Referring to FIGS. 2 and 5, the assembly of the second embodiment circuitry 24 within the sealed volume is described. First, the second embodiment circuitry 24 is electrically connected to the electrodes. These connections are on the interior side of electrode carrier surface 16 with respect to the sealed volume created by support frame 32 and electrode carrier surface 16. These connections were previously described. Then, the power source 84, such as a DC battery, is mounted externally on the topside of the support frame 32, preferably in a mount like battery holder 86. The double-pole, double-throw pressure sensitive switch 50 is mounted on the topside of the support frame 32 over a sealable aperture. Electrical connections 88 from the power source and pressure switch pass through sealable apertures in support frame 32 to the internal circuitry. All apertures are sealed, preferably with a silicone-type adhesive.

b. Description of Operation

Figure 1C:
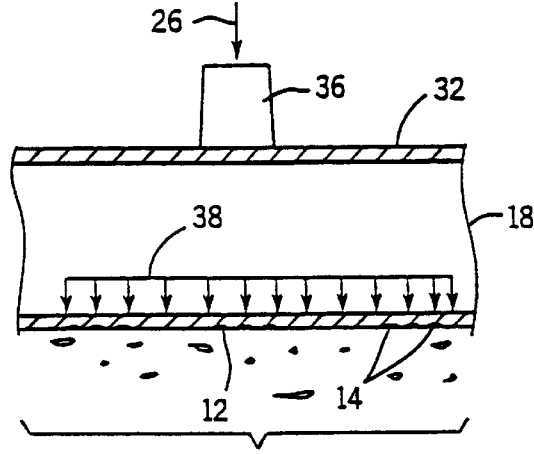
Figure 1D:
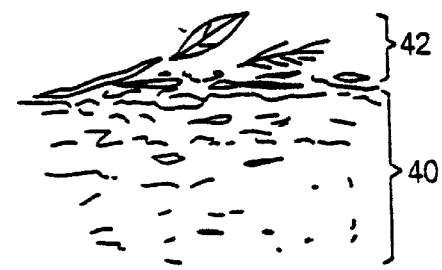

Referring generally to FIGS. 1c, 1d and 7, described is the measurement method specifically for determination of forest duff moisture content using the apparatus 10. For both embodiments, the area to be measured is prepared by sweeping away large forest debris 42 (shown in FIG. 1d) such as sticks, stones, other objects not of interest. Sweeping should leave a relatively flat, smooth duff layer. If necessary, the bellows system should now be inflated. Next, the apparatus 10 is placed electrode-side down on the prepared duff 40. Then the user applies a downward force to handle 36 until the moisture measurement circuitry 22 is activated, and maintains this force until measurement reading is complete. Measurement output differs depending on which embodiment of the invention has been used, and analysis appropriate to the output is used to determine moisture content.

FIG. 7 depicts a sample linear regression performed upon TDR moisture readings versus volumetric moisture content readings (TDR readings are from the second embodiment). This regression provides one with a calibration equation that is valid for materials of varying bulk density. A similar linear regression analysis may be performed using the numerical data from the first embodiment and volumetric moisture content.

It is thought that the moisture control apparatus of the present invention and many of its attendant advantages will be understood from the foregoing description and it will be apparent various changes may be made in the form, construction and arrangement thereof without departing from the spirit and scope of the invention or sacrificing all of its material advantages. For example, it will be apparent to one skilled in the art that moisture content measuring apparatus may be used for measuring the moisture content of a wide variety of materials, not just organic materials with air voids. In order to apprise of the various embodiments that may fall within the scope of the invention, the following claims are made:

We claim:

1. A method of measuring forest duff moisture content using a support frame, an electrode carrier surface, at least two electrodes, said electrodes affixed to the electrode carrier surface, a force sensitive coupling connecting the support frame and the electrode carrier surface permitting application of a predetermined biasing force of separation between the support frame and the electrode carrier surface when the electrode carrier surface is pressed against a compressible material to be measured, moisture measurement circuitry providing a stimulating electrical signal to the electrodes and making measurements of that signal to provide an indication of material moisture content in the proximity of the electrodes, and an output display connected to the moisture measurement circuitry displaying the indication of the material moisture content in the proximity of the electrodes which comprises:

(a) clearing and leveling with respect to the plane of said electrode carrier surface and the duff material to be measured, (b) inflating a bellows system, (c) contacting the electrodes to the cleared duff material, (d) pressuring the bellows system until the moisture measurement circuitry activates, and (e) maintaining activation pressure until measurement complete.

* * * * *